(12) United States Patent
Chiu et al.

(10) Patent No.: US 10,067,084 B2
(45) Date of Patent: *Sep. 4, 2018

(54) SOLID STATE SENSOR FOR METAL ION DETECTION AND TRAPPING IN SOLUTION

(71) Applicant: WaferTech, LLC, Camas, WA (US)

(72) Inventors: Re-Long Chiu, Vancouver, WA (US); Jason Higgins, Yacolt, WA (US)

(73) Assignee: WAFERTECH, LLC, Camas, WA (US)

( * ) Notice: Subject to any disclaimer, the term of this patent is extended or adjusted under 35 U.S.C. 154(b) by 348 days.

This patent is subject to a terminal disclaimer.

(21) Appl. No.: 14/663,278

(22) Filed: Mar. 19, 2015

(65) Prior Publication Data

US 2015/0192539 A1    Jul. 9, 2015

Related U.S. Application Data

(63) Continuation of application No. 12/848,860, filed on Aug. 2, 2010, now Pat. No. 9,000,783.

(51) Int. Cl.
| | |
|---|---|
| *G01N 27/414* | (2006.01) |
| *H01L 21/66* | (2006.01) |
| *G01N 27/07* | (2006.01) |

(52) U.S. Cl.
CPC .......... *G01N 27/414* (2013.01); *G01N 27/07* (2013.01); *H01L 22/10* (2013.01); *H01L 2924/0002* (2013.01)

(58) Field of Classification Search
CPC ...... G01N 27/414; G01N 27/07; H01L 22/10; H01L 2924/0002
See application file for complete search history.

(56) References Cited

U.S. PATENT DOCUMENTS

| | | |
|---|---|---|
| 4,963,815 A | 10/1990 | Hafeman |
| 5,545,517 A | 8/1996 | Thompson et al. |
| | (Continued) | |

OTHER PUBLICATIONS

Aguilar et al., "Chemical sensors using peptide-functionalized conducting polymer nanojunction arrays," *Applied Physics Letters*, 87(193108):1-3.

(Continued)

*Primary Examiner* — Maris R Kessel
(74) *Attorney, Agent, or Firm* — Duane Morris LLP (57) ABSTRACT

A device, apparatus and method for trapping metal ions and detecting metal ion contamination in a solution provide a semiconductor device formed on a semiconductor substrate and including an N-well formed over a P-type substrate and at least a contact portion of the N-well in electrical contact with the solution. When the semiconductor device is optically illuminated, a P/N junction is formed as a result of photovoltaic phenomena. Metal ions from the solution migrate to the contact area due to the voltage created at the P/N junction. The semiconductor device includes a conductive structure with conductive features separated by a gap and therefore in an initially electrically open state. When the ions migrate to the contact area, they precipitate, at least partially bridging the gap and creating conductance through the conductive structure. The conductance may be measured to determine the amount of metal ion contamination.

20 Claims, 5 Drawing Sheets

(56) References Cited

U.S. PATENT DOCUMENTS

| | | | |
|---|---|---|---|
| 5,900,136 A | 5/1999 | Gotsu et al. | |
| 7,241,699 B2 * | 7/2007 | Van Zeghbroeck | H01L 21/0445 257/E21.054 |
| 8,038,947 B2 | 10/2011 | Thompson | |
| 8,263,410 B2 * | 9/2012 | Kang | G01N 21/554 356/337 |
| 2002/0036146 A1 | 3/2002 | Akutsu et al. | |
| 2008/0211040 A1 * | 9/2008 | Lieber | B82Y 10/00 257/414 |
| 2008/0230804 A1 * | 9/2008 | Nishi | H01L 21/28518 257/190 |
| 2008/0237674 A1 * | 10/2008 | Ueda | H01L 21/823418 257/300 |
| 2009/0221086 A1 * | 9/2009 | Ha | G01N 21/31 436/164 |

OTHER PUBLICATIONS

Chiu et al., "S/D LDD junction stain/delineation by electrochemical displacement with illumination," *Proceedings from the 34th International Symposium for Testing and Failure Analysis (ISTFA)*, Nov. 2-6, 2008, Portland, OR, pp. 163-167.

Kim et al., "Fabrication of submicron size electrode via nonetching method for metal ion detection," *Applied Physics Letters*, 2005, 86(073113):1-3.

Petrov et al., "Metal-ion detection by the magnetic-field-sensitive fluorescence of intramolecular exciplexes containing aza-crown-ether moieties as electron donor," *J. Phys. Chem. A*, 1997, 101:7043-7045.

Sgammato et al., "Detection of divalent transition metal ions in complex media by capillary electrophoresis," *Proceedings of the 12th Annual Conference on Hazardous Waste Research*, Erickson et al., eds., 1997, Kansas State University, Manhattan Kansas, pp. 195-202.

Shepard et al., "Heavy metal ion detection using peptide-modified hydrogel layers on a quartz crystal microbalance," *Meeting of the American Institute of Chemical Engineers*, Oct. 30-Nov. 4, 2005, Cincinnati, OH, 8 pages.

Sugunan et al., Heavy-metal ion sensors using chitosan-capped gold nanoparticles, *Science and Technology of Advanced Materials*, 2005, 6:335-340.

Supino et al., "Micromachined particles for detecting metal-ion concentration in fluids," *IEEE Journal of Microelectromechanical Systems*, Oct. 2006, 15(5):1299-1307.

Xu et al., "In situ spectroelectrochemical study of quercetin oxidation and complexation with metal ions in acidic solutions," *Bull. Korean Chem. Soc.*, 2007, 28(5):889-892.

* cited by examiner

SOLID STATE SENSOR FOR METAL ION DETECTION AND TRAPPING IN SOLUTION

RELATED APPLICATION

This application is a continuation of U.S. patent application Ser. No. 12/848,860, filed on Aug. 2, 2010, the contents of which are hereby expressly incorporated by reference as if set forth in their entirety.

TECHNICAL FIELD

The present invention relates to a device, apparatus and method for the analysis and detection of metal ions in a solution. The device, apparatus and method of the invention are further directed to the removal of metal ions from solution via metal ion trapping.

BACKGROUND

In today's advanced semiconductor manufacturing industry, it is of critical importance to prevent contamination in all processing operations and also to detect contamination and identify the type and source of contamination as soon as possible. This applies to wet chemistry processing operations as well as all other operations used to manufacture semiconductor devices such as dry chemical processing, chemical mechanical polishing (CMP), plasma processing operations, thin film deposition operations, photolithographic operations, wafer transport operations and the like.

In wet chemical processing solutions or in other operations in which a chemical cleaning and/or rinsing solution is used, metal ion contamination in the solution must be identified as quickly as possible. The metal ion contamination in the solution contaminates and can destroy the devices being processed in the solution and metal ion contamination is also indicative of a processing problem. In addition to the metal ion contamination causing shorting or particle contamination of the device being processed in the solution, the contamination may result in ineffectiveness of the solution in carrying out its intended function. Metal ion contamination may further be indicative of a degradation of a processing tool such as the erosion of a metal part from which the metal ions emanate. This degradation can cause other equipment problems such as electrical problems and further contamination issues. If the metal ion contamination goes undetected, additional devices become contaminated as they undergo processing and the cause of the contamination may become exacerbated. The presence, extent and source of the metal ion contamination must be determined in order to eliminate the problem.

It would therefore be advantageous to detect metal ion contamination as soon as possible in order to prevent contamination of multiple devices over time and to minimize the degradation of processing equipment which can result in device misprocessing and further contamination.

Spectroscopic analytical techniques such as atomic absorption or fluorimetry are available to analyze metal ion contamination in a sampling solution. These techniques, however, are time dependent and also depend on the loading effect in the solution and human error. Moreover, the results obtained using these techniques are not real-time, in-situ results.

The present invention addresses these shortcomings of present techniques for monitoring and detecting metal ion contamination in solutions.

SUMMARY

To address these and other needs and in view of its purposes, the disclosure provides, according to one aspect, a method for detecting metal ions in a solution.

The method includes providing a semiconductor device contacting a solution, the semiconductor device comprising at least one area of N-type material, such as an N-well area over a P-type material with at least one contact part of the at least one N-well area in electrical contact with the solution. The method further provides optically illuminating the semiconductor device thereby creating a P/N junction and causing metal ions of the solution to migrate to the at least one contact part. The method further provides monitoring conductance of a structure of the semiconductor device having a conductance that varies with an amount of metal ions accumulated on the semiconductor device and calculating a concentration of metal ions in the solution, based on the conductance.

According to another aspect, a method for removing metal ions from a solution is provided. The method comprises providing a semiconductor device contacting a solution, the semiconductor device comprising at least one N-type material area over a P-type material with at least one contact part of the at least one N-type material area in electrical contact with the solution, optically illuminating the semiconductor device thereby creating a P/N junction and causing metal ions of the solution to become trapped at the at least one contact part and monitoring conductance of a structure of the semiconductor device having a conductance that varies with an amount of the metal ions trapped at said at least one contact part.

According to another aspect, an apparatus for in-situ detection of metal ion contamination in a solution, is provided. The apparatus includes a vessel containing a solution, a semiconductor device formed on a substrate and disposed in the solution, the semiconductor device comprising at least one N-well area over a P-type material with at least one contact part of the at least one N-well area in electrical contact with the solution. The apparatus also includes an illumination source arranged such that the semiconductor device is exposed to the illumination source. Electrical circuitry is coupled to the semiconductor device and capable of testing at least one of conductance and resistance of the semiconductor device.

According to another aspect, a method for detecting metal ions in a solution, is provided. The method comprises: providing a semiconductor device contacting a solution, the semiconductor device comprising at least one N-type material layer oriented in a first direction and covering a P-type material layer oriented in the first direction, and metal leads formed over the N-type material layer and separated from one another by a gap filled with a dielectric and from portions of the N-type material layer by the dielectric; optically illuminating the semiconductor device thereby creating a voltage across a P/N junction and causing metal ions of the solution to migrate to, and at least partially bridge, the gap. The method further comprises calculating a concentration of the metal ions in the solution, based on conductance of the semiconductor device.

According to another aspect, a method for detecting metal ion concentration in a solution, is provided. The method comprises: providing a semiconductor device contacting a solution, the semiconductor device comprising a plurality of pairs of composite structures, each of the pair of composite structures including two electrically isolated composite structures spaced apart by a gap filled with a dielectric, each composite structure including a conductive material disposed on an N-type material segment formed of an N-type material layer that covers a P-type material layer and wherein the pairs of composite structures include pairs in which the two electrically isolated composite structures are spaced apart by different gap distances. The method further comprises optically illuminating the semiconductor device thereby creating a voltage across a P/N junction and causing metal ions of the solution to bridge at least one of the gaps and create a conductive path between composite structures of at least one of the pairs of composite structures. The method further comprises monitoring concentration of the metal ions in the solution by measuring conductance of the pairs of composite structures, wherein the concentration varies with a greatest gap distance across which a conductive path exists.

According to another aspect, an apparatus for in-situ detection of metal ion contamination in a solution, is provided. The apparatus comprises: a vessel containing a solution and a semiconductor device contacting the solution. The semiconductor device comprises at least one N-type material layer oriented in a first direction and covering a P-type material layer oriented in the first direction, metal leads formed over the N-type material layer and separated from one another by a gap filled with a dielectric and from portions of the N-type material layer by the dielectric. The apparatus further comprises an illumination source adapted to expose the semiconductor device to illumination; and electrical circuitry coupled to a structure of the semiconductor device and adapted to determine if a conductive path of metal ions from the solution, exists between the metal leads and across the gap.

According to yet another aspect, the device, apparatus and method of the disclosure can be used to trap metal ions, thereby removing metal ions from a solution and reducing contamination levels in the solution.

BRIEF DESCRIPTION OF THE DRAWING

The disclosure is best understood from the following detailed description when read in conjunction with the accompanying drawing. It is emphasized that, according to common practice, the various features of the drawing are not necessarily to scale. On the contrary, the dimensions of the various features are arbitrarily expanded or reduced for clarity. Like numerals denote like features throughout the specification and drawing.

FIGS. 4A-4C correspond to FIGS. 5A-5C.

DETAILED DESCRIPTION

Provided is a metal ion detection device and method that can be used for in-situ detection of metal ion contamination in a solution and also for metal ion trapping, i.e. causing the metal ions to be drawn from the solution.

The metal ion detection device is a self-powered optical sensor array that is used for in-situ detection of metal ion contamination in solution. The detection device is sensitive enough to monitor metal ions before the concentration of metal ion contamination reaches a dangerous level, providing early warning and prevention of problems associated with metal ion contamination and pollution.

The metal ion detection device includes a semiconductor device with at least one area of N-type material, such as an N-well area, over a P-type material such as a P-type substrate and utilizes a photovoltaic operation to optically illuminate the semiconductor device creating a P/N junction with a voltage across the P/N junction. The creation of the P/N junction causes the N-well to act as a cathode drawing positive metal ions from the solution to the cathode. The device includes at least one contact area of the N-well that is electrically exposed to or coupled to, the solution. The metal ions are attracted to the contact area which may be an opening in a dielectric layer formed over the N-well or a conductive contact extending through a dielectric and which contacts both the N-well contact area and the solution. The semiconductor device also includes conductive features that essentially form a conductive structure that includes a gap and therefore an electrical open, upon formation. The conductive structure is situated such that, when the metal ions from the solution are attracted to the N-well contact area, the metal ions precipitate at the cathode and at least partially bridge the gap forming a closed circuit. In some exemplary embodiments, the semiconductor device may include multiple conductive structures, i.e. multiple arrangements of pairs of conductive features such that the gaps between the corresponding pairs of conductive features are of different dimensions. In some embodiments, an array of such conductive structures may be used.

An electrical circuit is coupled to the conductive structure or structures and measures conductance and/or resistance. The conductance and resistance is a function of the amount of metal ion precipitates present and which have bridged the gap. When multiple conductive structures with different gap spacings are used, the initial conductance of the conductive structures will be a function of the gap dimensions and conductance across larger gaps will be indicative of greater levels of metal ion contamination and precipitation. The monitoring may be done in-situ with the semiconductor device immersed in or at least contacting the solution and coupled to the electrical circuit.

According to some exemplary embodiments, the metal ion precipitates collected at the contact part of the N-well on the semiconductor device, may be further analyzed for elemental composition using Energy Dispersive X-rays (EDX), a Scanning Electron Microscope (SEM) or other conventional techniques for performing elemental analyses. After the concentration and/or elemental composition of the metal ions is determined, the source of the metal ions may therefore be identified and corrective action will be taken to address the source of the metal ion contamination and correct the problem causing the contamination.

According to other embodiments, the metal ion detection device may be used to remove metal ions from solution via trapping, using the same techniques described supra and infra.

Figure 1:
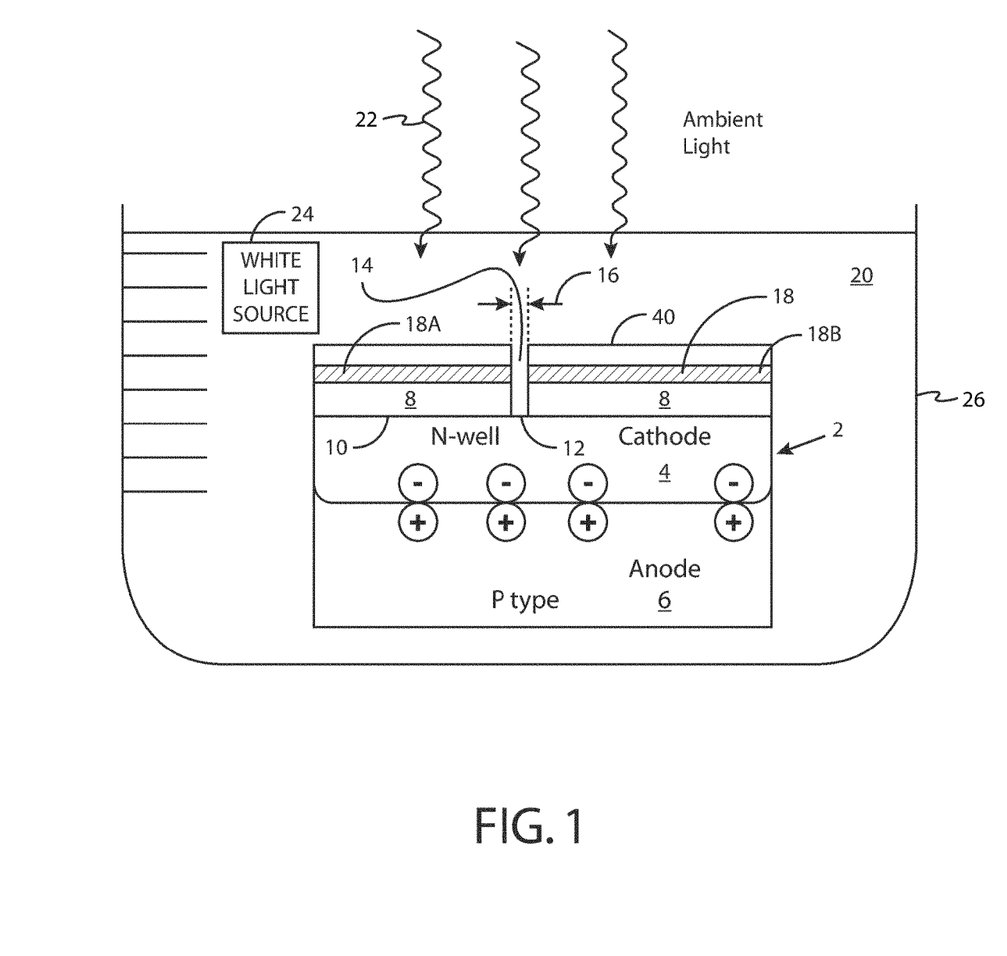
FIG. 1 is a cross-sectional view of a semiconductor device in an apparatus according to various embodiments of the disclosure.

FIG. 1 shows semiconductor device 2 within solution 20 maintained within vessel 26. According to the exemplary illustrated embodiment, semiconductor device 2 includes an area of N-type material, such as N-well 4, formed over P-type material 6. According to one exemplary embodiment, P-type material 6 is a P-type semiconductor substrate with N-well 4 being an N-type semiconductor material formed in the substrate according to conventional methods. In other exemplary embodiments, N-well 4 may take on other forms and may be formed over P-type material 6 in other arrangements and over other substrates but will be referred to as N-well 4 throughout the description. N-well 4 may be an N+ type material. Semiconductor device 2 includes dielectric layer 8 formed over substantially top surface 10 of N-well 4. Dielectric layer 8 is advantageously a transparent material and may be formed of any of various suitable dielectric materials and top surface 10 is substantially planar. Opening 14 extends through dielectric layer 8 exposing contact area 12 of N-well 4 directly to solution 20. Conductive structure 18 is formed over dielectric 8 but includes a gap located at opening 14. The gap leaves separated portions of conductive structure 18 spaced apart by distance 16. In the illustrated arrangement, conductive structure 18 consists of a pair of conductive leads 18A and 18B spaced apart by a gap of spacing 16. Conductive material 18 may be a metal such as tungsten, copper, aluminum or other suitable metals. Spacing 16 may advantageously range from 0.1 microns to 1 micron wide in one exemplary embodiment or it may range from 0.01 microns to 1000 microns in various exemplary embodiments but still other spacings may be used in other exemplary embodiments. Passivation layer 40 may optionally be formed over conductive leads 18A and 18B using conventional techniques and materials to minimize corrosion of the conductive leads 18A and 18B in solution 20.

Solution 20 may be any of various solutions used in semiconductor manufacturing. Solution 20 may be a solution disposed within a wet bench for wet bench processing or it may represent an effluent solution from a semiconductor processing operation or from a cleaning operation. In some embodiments, solution 20 may represent a processing solution and in other exemplary embodiments solution 20 may be a cleaning fluid used to clean wet or dry processing tools. In one exemplary embodiment, solution 20 may be an effluent slurry solution used in a chemical mechanical planarization (CMP) operation and according to another exemplary embodiment, solution 20 may be a fresh slurry solution prior to use as a CMP or other operation. Solution 20 may be a stagnant solution in any of various baths or it may be a dynamic solution in a recalculating, cascading or other type bath or a fresh solution to be used in a processing operation. Vessel 26 may be any of various vessels or containers capable of holding a solution such as in a wet bench or other wet processing tool. Vessel 26 may retain an effluent stream from a CMP tool, in one exemplary embodiment. According to other exemplary embodiments, vessel 26 may be a pipe or other conduit that includes a solution therein.

Semiconductor device 2 is then exposed to optical illumination which may be ambient light 22 as illustrated in FIG. 1. Ambient light 22 may be sunlight or room light. In other exemplary embodiments, another white light source such as white light source 24 may be arranged either in or out of solution 20 to illuminate semiconductor device 2 and create a P/N junction such as illustrated in FIG. 1.

Figure 2:
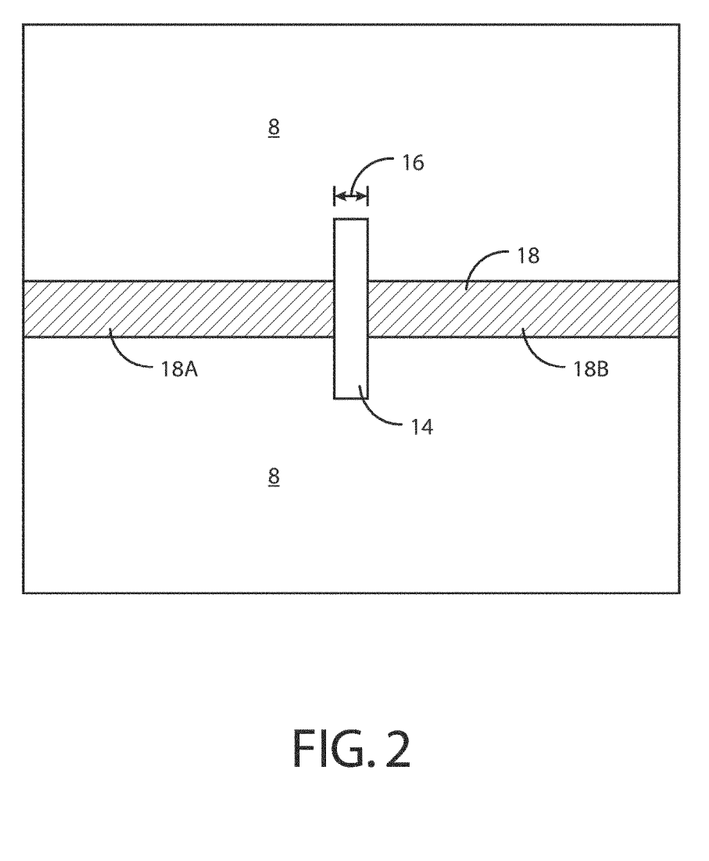
FIG. 2 is a top, plan view of a semiconductor device according to various embodiments of the disclosure.

Now referring to FIG. 2, it can be seen that, although conductive structure 18 may be a reflective material such as a metal which may optionally be covered with a passivation layer, the bulk of semiconductor structure 2 is exposed to the illumination sufficient to create a P/N junction by way of photovoltaic operation. The surface area covered by conductive structure 18 is small compared to the surface area of the N-well 4 that is covered by transparent dielectric 8 and thereby exposed to illumination from the illumination source. The photovoltaic operation creates the anode/cathode arrangement such as illustrated in FIG. 1.

Referring to FIGS. 1 and 2, electrical circuitry (not shown in FIGS. 1 and 2 but shown in FIG. 3) is coupled to opposed ends of conductive structure 18 and measures resistance or conductance along conductive structure 18. Initially, because conductive leads 18A and 18B are spaced apart by spacing 16 and therefore conductive structure 18 is discontinuous, conductance will be essentially zero and resistance will be essentially infinite. When the P/N junction becomes optically illuminated, metal ions from solution 20 migrate toward contact area 12 of N-well 4. More particularly, the metal ions precipitate at the contact area 12 of the cathode formed by the photovoltaic creation of the P/N junction. In doing so, the metal ion precipitates fill the gap represented by spacing 16 and enable conductance between conductive leads 18A and 18B and completion of a circuit of conductive structure 18. Conventional circuitry can be used to measure conductance/resistance. The metal ion concentration in the solution is determined according to the following relationship:

$$\text{Metal ion conc.} = f(\text{exposure time}, 1/R).$$

Exposure time represents the time in which the photovoltaically activated P/N junction is exposed to the solution. Conductance/resistance may be measured as a function of exposure time and various data correlations may be established or other data analysis techniques used, to determine the metal ion concentration in solution 20 based upon the amount of metal ion precipitates bridging the gap between conductive leads 18A and 18B and therefore the conductance/resistance. According to various exemplary embodiments, the testing and therefore determination of metal ion concentration can be performed in-situ when semiconductor device 2 is within solution 20. If further analysis is needed, semiconductor device 2 may be removed from the solution and the identification of metal elements can be determined by SEM or EDX or other suitable elemental analytical techniques.

Figure 3:
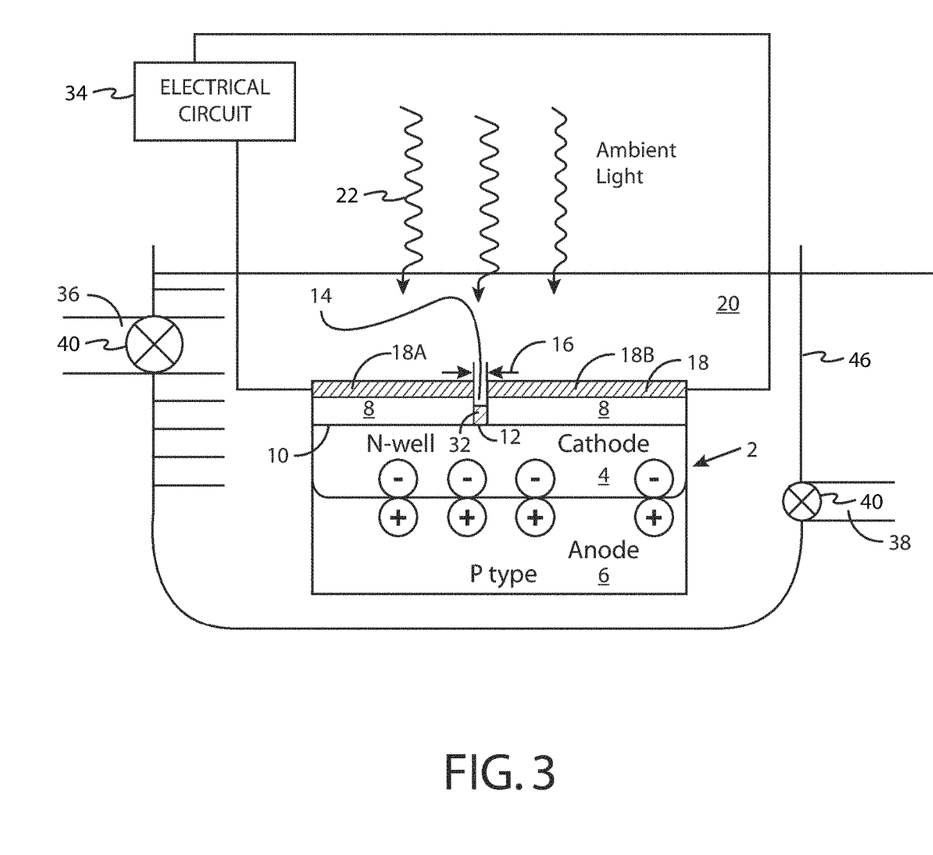
FIG. 3 is a cross-sectional view of another semiconductor device and another apparatus according to various embodiments of the disclosure.

FIG. 3 shows another exemplary semiconductor device and apparatus arrangement according to various embodiments of the disclosure. FIG. 3 is similar to FIG. 1 but according to the exemplary embodiment illustrated in FIG. 3, semiconductor device 2 includes conductive plug 32 formed in opening 14 at contact area 12. Conductive plug 32 may be formed of various suitable materials including but not limited to tungsten. Optional passivation layer 40 may be formed over conductive leads 18A and 18B but is not shown in FIG. 3. The dimensions of opening 14 and the thickness of dielectric layer 8 and plug 32 may be chosen such that conductive leads 18A and 18B are not in electrical contact before the method of the disclosure causes metal ions to migrate toward contact area 12 as precipitates and contact conductive plug 32. FIG. 3 also illustrates vessel 46 to be a re-circulating or other dynamic bath including inlet 36 outlet 38 each with valves 40. Further illustrated in FIG. 3 is electrical circuit 34 coupled to each of conductive leads 18A and 18B and which includes electrical circuitry capable of measuring at least conductance and resistance between conductive leads 18A and 18B.

Figures 4A, 4B, 4C, 5A, 5B, 5C:
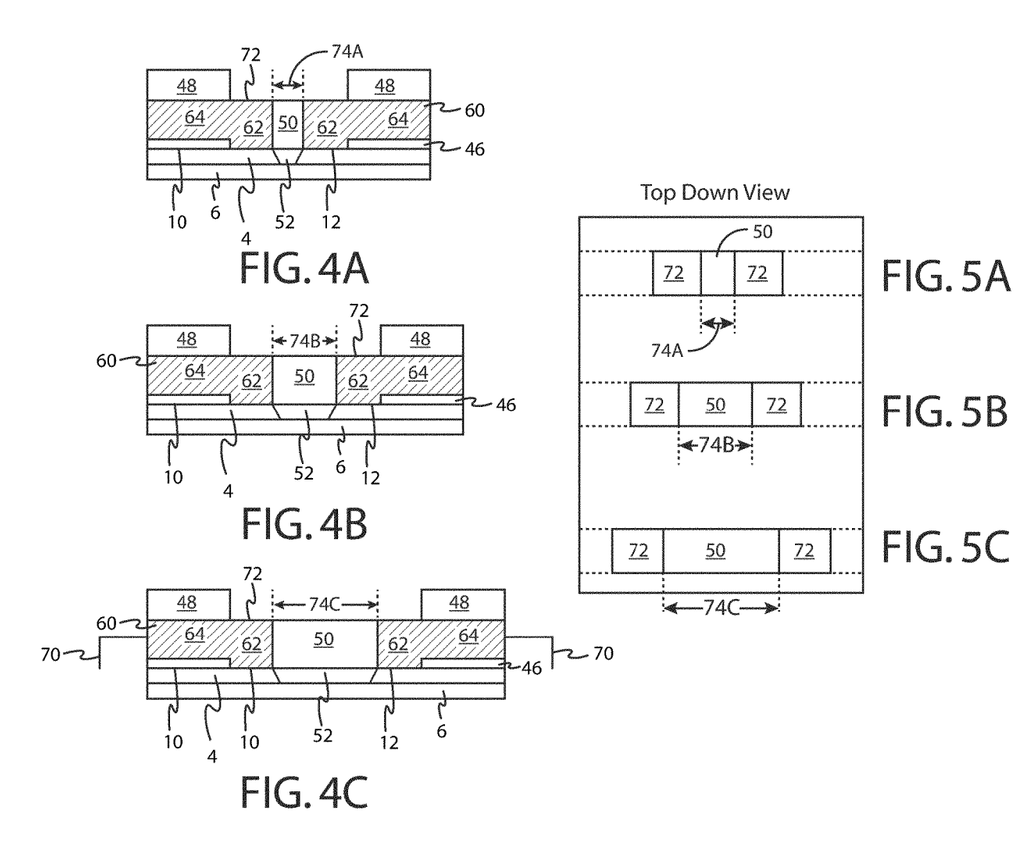
FIGS. 4A-4C are cross-sectional views of semiconductor devices according to various embodiments of the disclosure and FIGS. 5A-5C are corresponding top plan views.

FIGS. 4A-4C represent cross-sectional views of another embodiment of the semiconductor device according to various embodiments of the disclosure and correspond to top plan views shown in FIGS. 5A-5C, i.e. the structure shown in cross-section in FIG. A is also shown in top plan view in FIG. A.

In each of FIGS. 4A-4C, N-well 4 is formed over P-type material 6. N-well 4 includes substantially planar top surface 10 and it can be seen that N-well 4 is separated into electrically isolated sections. Dielectric materials 46, 48 and 50 are disposed over top surface 10 and are advantageously transparent dielectric materials. Various suitable dielectric materials may be used. Dielectric material 50 includes lower section 52 that extends through N-well 4 thereby electrically isolating the sections of N-well 4 from one another. Conductive structure 60 includes a duality of conductive plugs 62, each laterally coupled to a corresponding conductive lead 64. Conductive plug 62 electrically couples contact area 12 of N-well 4, to solution 20. Conductive leads 64 are coupled to an electrical circuit (not shown) via wires 70. When semiconductor device 2 is optically illuminated, photovoltaically creating a P/N junction between N-well 4 and P-type material 6, metal ions in solution migrate to contacts 72 and precipitate there. It can be seen that contacts 72 are spaced apart by respective gaps 70A, 70B and 74C in FIGS. 4A-4C. Although various device features are arbitrarily expanded or reduced for clarity, FIGS. 4A-4C and 5A-5C illustrate that the respective contacts 62 in FIGS. 5A through 5C shown as formed on one substrate, include increasingly larger gaps represented by 74A, 74B, 74C. Considering FIGS. 5A-5C successively, the metal ion precipitates would necessarily have to bridge an increasingly larger gap in order to enable conductance along the initially isolated respective conductive structures represented by conductive plugs 62 and conductive leads 64, thus requiring a higher amount of metal ion precipitates and thus a higher metallic concentration to bridge the gap.

Figure 6:
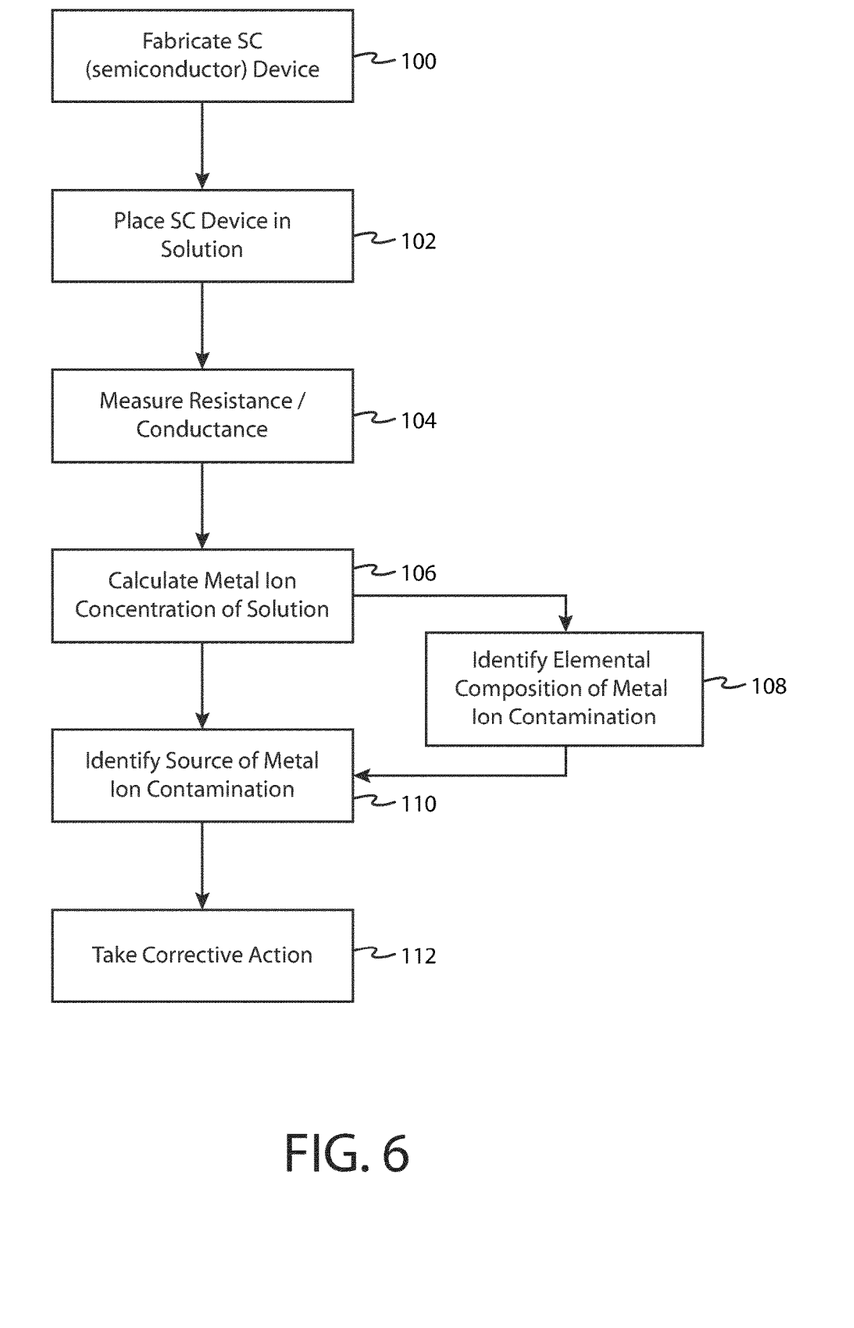
FIG. 6 is a flowchart illustrating an exemplary method according to various embodiments of the disclosure.

FIG. 6 is a flowchart illustrating an exemplary method of various embodiments of the disclosure. At step 100, the semiconductor device such as any of the semiconductor devices described or illustrated herein and variations thereof, is fabricated. The semiconductor device is placed in solution at step 102 and this may include immersing the device in a solution and/or affixing the semiconductor device to one of the aforementioned vessels of the disclosure. At step 104, resistance and/or conductance is measured as described previously and at step 106, metal ion concentration of the solution is calculated. Optional step 108 includes identifying the elemental composition of the metal ion contamination such as by using an SEM, EDX or other suitable analytic methods and at step 110, the source of the metal ion contamination is identified. At step 112, corrective action is taken. The corrective action may include reverse engineering, analysis or modification of various semiconductor processing tools, or various other suitable measures.

The preceding merely illustrates the principles of the disclosure. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of various embodiments of the disclosure and the concepts contributed by the inventors to furthering the art, and are to be construed as being without limitation to such specifically recited examples and conditions. Moreover, all statements herein reciting principles, aspects, and embodiments of the disclosure, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, unless expressly described otherwise.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents.

What is claimed is:

1. A method for detecting metal ions in a solution, said method comprising:
    providing a semiconductor device contacting said solution, said semiconductor device comprising:
        at least one N-type material layer oriented in a first direction and covering a P-type material layer oriented in said first direction,
        metal leads formed over said N-type material layer and separated from one another by a gap filled with a dielectric, and
        portions of said N-type material layer being separated from each other by said dielectric;
    optically illuminating said semiconductor device, thereby creating a voltage across a P/N junction and causing metal ions of said solution to at least partially bridge said gap by migrating to and precipitating upon said metal leads and upon said dielectric; and
    calculating a concentration of said metal ions in said solution, based on conductance of said semiconductor device.

2. The method as in claim 1, wherein each of said metal leads directly contacts a respective portion of said N-type material at locations adjacent said gap, said respective portions separated by said gap filled with said dielectric.

3. The method as in claim 1, wherein said conductance comprises conductance between said metal leads and further comprising monitoring said conductance.

4. The method as in claim 1, wherein said solution comprises an effluent stream from a semiconductor processing operation and said optically illuminating comprises exposing said semiconductor device to ambient light.

5. The method as in claim 1, wherein said optically illuminating comprises exposing said semiconductor device to a white light source disposed in said solution and said calculating a concentration takes place when said semiconductor device contacts said solution.

6. The method as in claim 1, further comprising identifying an elemental composition of said metal ions using at least one of Scanning Electron Microscope (SEM) and Energy Dispersive X-ray (EDX), and taking corrective action in a semiconductor manufacturing operation, based on said elemental composition of said metal ions.

7. The method as in claim 1, wherein said semiconductor device further includes a further dielectric disposed over said metal leads, said further dielectric including openings therethrough, that expose said gap and respective ends of said metal leads adjacent said gap.

8. The method as in claim 1, wherein said gap extends through said N-type material layer.

9. A method for detecting metal ion concentration in a solution, said method comprising:
provided a semiconductor device contacting said solution, said semiconductor device comprising a plurality of pairs of composite structures, each said pair of composite structures including two electrically isolated composite structures spaced apart by a gap filled with a dielectric, each said composite structure including a conductive material disposed on an N-type material segment formed of an N-type material layer disposed over a P-type material layer and wherein said pairs of composite structures include pairs in which said two electrically isolated composite structures are spaced apart by different gap distances;
optically illuminating said semiconductor device thereby creating a voltage across P/N junctions and causing metal ions of said solution to bridge at least one said gap and create a conductive path between composite structures of at least one said pair of composite structures; and
monitoring concentration of said metal ions in said solution by measuring, conductance of said pairs of composite structures, wherein said concentration varies with a greatest gap distance across which a conductive path exists.

10. The method as in claim 9, wherein said providing a semiconductor device further comprises disposing a further dielectric over said plurality of pairs of composite structures, said further dielectric including openings that expose said gaps and respective ends of each of said pairs of composite structures adjacent said gap.

11. The method as in claim 9, wherein said optically illuminating comprises exposing said semiconductor device to ambient light.

12. The method as in claim 9, wherein said optically illuminating comprises exposing said semiconductor device to a white light source disposed in said solution and wherein said optically illuminating and said measuring conductance take place when said semiconductor device contacts said solution.

13. The method as in claim 9, wherein said providing a semiconductor device includes said conductive material comprising tungsten and further comprising analyzing elemental composition of said metal ions.

14. A method comprising:
contacting a solution with a semiconductor device, said semiconductor device comprising at least one N-type material layer covering a P-type material layer, and metal leads formed over said N-type material layer and separated from one another by a gap filled with a dielectric, wherein said N-type material layer includes discrete portions separated by the gap filled with said dielectric; and
optically illuminating said semiconductor device, thereby creating a voltage across a P/N junction and causing metal ions of said solution to at least partially bridge said gap by migrating to and precipitating upon said metal leads and upon said dielectric.

15. The method as in claim 14, further comprising:
calculating a concentration of said metal ions in said solution based on conductance of said semiconductor device, wherein said conductance comprises conductance between said metal leads; and
monitoring said conductance.

16. The method as in claim 14, further comprising:
exposing said semiconductor device to a white light source disposed in said solution.

17. The method as in claim 14, further comprising:
identifying an elemental composition of said metal ions using at least one of Scanning Electron Microscope (SEM) and Energy Dispersive X-ray (EDX); and
taking corrective action in a semiconductor manufacturing operation, based on said elemental composition of said metal ions.

18. The method as in claim 14, wherein each of the metal leads directly contacts a respective portion of said N-type material layer at locations adjacent said gap, said respective portions separated by said gap filled with said dielectric.

19. The method as in claim 14, further comprising:
exposing said semiconductor device to ambient light.

20. The method as in claim 14, wherein said gap extends through said N-type material layer.

* * * * *